United States Patent

Mills et al.

[11] Patent Number: 6,126,971
[45] Date of Patent: *Oct. 3, 2000

[54] STABLE ORAL CI-981 FORMULATION AND PROCESS FOR PREPARING SAME

[75] Inventors: Nancy Mills, Mt. Arlington; Nouman A. Muhammad, Long Valley; Jay Weiss, East Brunswick; Russell U. Nesbitt, Somerville, all of N.J.

[73] Assignee: Warner-Lambert Company, Morris Plains, N.J.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/886,982

[22] Filed: Jul. 2, 1997

Related U.S. Application Data

[63] Continuation of application No. 08/246,919, May 20, 1994, Pat. No. 5,686,104, which is a continuation of application No. 08/005,708, Jan. 19, 1993, abandoned.

[51] Int. Cl.[7] .................................................. A61K 47/02
[52] U.S. Cl. ........................................... 424/484; 514/970
[58] Field of Search ........................... 424/484, 692–693, 424/715; 514/824, 970

[56] References Cited

U.S. PATENT DOCUMENTS

| | | | |
|---|---|---|---|
| 4,681,893 | 7/1987 | Roth et al. ............................... | 514/422 |
| 5,030,447 | 7/1991 | Joshi et al. ................................. | 424/80 |
| 5,686,104 | 11/1997 | Mills et al. ............................... | 424/451 |

FOREIGN PATENT DOCUMENTS 0 409 281 A1  1/1991  European Pat. Off. .

*Primary Examiner*—Edward J. Webman
*Attorney, Agent, or Firm*—Merchant & Gould P.C.

[57] ABSTRACT

An oral pharmaceutical composition is provided for treating hypercholestereolemia or hyperlipidemia containing an advantageous formulation for stabilizing the HMG-CoA coenzyme A inhibitor, CI-981 Hemi-Calcium, of formula (IA)

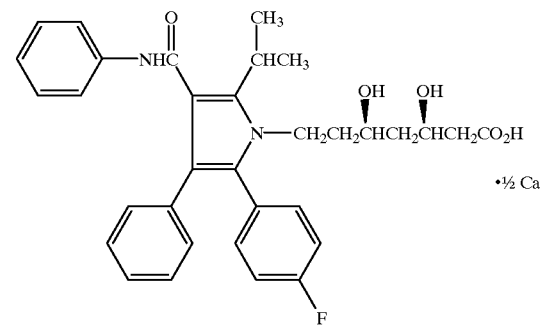

with effective amounts of calcium carbonate.

A method for preparing a CI-981 stabilizing composition is described.

19 Claims, No Drawings

STABLE ORAL CI-981 FORMULATION AND PROCESS FOR PREPARING SAME

This application is a continuation of Ser. No. 08/246,919 filed May 20, 1994 now U.S. Pat. No. 5,686,104, which is a continuation of Ser. No. 08/005,708 filed Jan. 19, 1993 now abandoned.

FIELD OF THE INVENTION

The present invention relates to stable oral pharmaceutical formulations of acid-sensitive substituted pyran ring-opened acid forms of substituted pyrrolyl carboxamides useful in the treatment of hypercholesterolemia or hyperlipidemia. A method for the preparation of such formulations is also described.

BACKGROUND OF THE INVENTION

Hypercholesterolemia and hyperlipidemia, conditions of excessively high levels of blood cholesterol and lipids, are well recognized risk factors in the onset of atherosclerosis and coronary heart disease. The blood cholesterol pool is generally dependent on dietary uptake of cholesterol from the intestine and biosynthesis of cholesterol throughout the body, especially the liver. Cholesterol is an indispensable component of virtually all cell membrane systems, as well as a precursor of a variety of steroid hormones and bile acids.

It is well known that inhibitors of 3-hydroxy-3-methylglutaryl-coenzyme A reductase (HMG-CoA reductase), an important enzyme catalyzing the intracellular synthesis of cholesterol, will bring about reduced levels of blood cholesterol, especially in terms of the low density lipoprotein form of cholesterol. Therefore, HMG-CoA reductase enzyme inhibitors are considered potentially useful as hypocholesterolemic or hypolipidemic agents.

Certain trans-6-[2-(3 or 4-carboxamido-substituted pyrrol-1-yl)alkyl]-4-hydroxypyran-2-ones and corresponding pyran ring-opened hydroxy acids derived therefrom have been described in U.S. Pat. No. 4,681,893 to Roth as potent inhibitors of HMG-CoA reductase which description is herewith incorporated by reference in the present specification. The pyran ring-opened hydroxy acids which are intermediates in the synthesis of the lactone compounds can be used as free acids or as pharmaceutically acceptable metal or amine salts. In particular, these compounds can be represented by the formula I below:

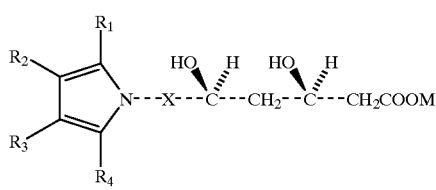

(I)

wherein X is —$CH_2$—, —$CH_2CH_2$—, —$CH_2CH_2CH_2$— or —$CH_2CH(CH_3)$—;

$R_1$ is 1-naphthyl; 2-naphthyl; cyclohexyl; norbornenyl; 2-,3-, or 4-pyridinyl; phenyl; phenyl substituted with fluorine, chlorine, bromine, hydroxyl, trifluoromethyl, alkyl of from one to four carbon atoms, alkoxy of from one to four carbon atoms, or alkanoylalkoxy of from two to eight carbon atoms;

either $R_2$ or $R_3$ is ——$CONR_5R_6$ where $R_5$ and $R_6$ are independently hydrogen; alkyl of from one to six carbon atoms; 2-,3-, or 4-pyridinyl; phenyl; phenyl substituted with fluorine, chlorine, bromine, cyano, trifluoromethyl, or carboalkoxy of from three to eight carbon atoms; and the other of $R_2$ or $R_3$ is hydrogen; alkyl of from one to six carbon atoms; cyclopropyl; cyclobutyl; cyclopentyl; cyclohexyl; phenyl; or phenyl substituted with fluorine, chlorine, bromine, hydroxyl, trifluoromethyl, alkyl of from one to four carbon atoms, alkoxy of from one to four carbon atoms, or alkanoyloxy of from two to eight carbon atoms;

$R_4$ is alkyl of from one to six carbon atoms; cyclopropyl; cyclobutyl; cyclopentyl; cyclohexyl; or trifluoromethyl; and M is a pharmaceutically acceptable salt, which includes a pharmaceutically acceptable metal salt or a pharmaceutically acceptable amine salt.

Among the stereo-specific isomers one particular compound having HMG-CoA reductase inhibitory activity, CI-981 Hemi-Calcium, is currently under development for the treatment of moderate to severe familial or nonfamilial hypercholesterolemia (Type IIa). This most preferred compound characterized is the ring-opened form of (2R-trans)-5-(4-fluorophenyl)-2-(1 methylethyl)-N,4-diphenyl-1-[2-(tetrahydro-4-hydroxy-6-oxo-2H-pyran-2-yl)ethyl]-1H-pyrrole-3-carboxamide, namely, the enantiomer [R-(R*, R*)]-2-(4-fluorophenyl)-β,δ-dihydroxy-5-(1-methylethyl)-3-phenyl-4-[(phenylamino)carbonyl)]-1H-pyrrole-1-heptanoic acid hemicalcium salt. Its chemical structure may be represented by formula IA:

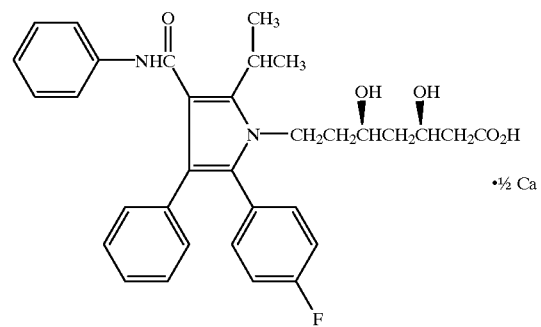

(IA)

The specific isomer (CI-981) has been described in U.S. Pat. No. 5,273,995.

However, these compounds are unstable in that they are susceptible to heat, moisture, low pH environment, and light. In an acidic environment, in particular, the hydroxy acids will degrade to lactone. In addition, the hydroxy acids will decompose rapidly when exposed to UV or fluorescent light.

When packaged in the form of tablets, powders, granules, or within capsules, the compounds may be further destabilized by contact with the molecular moieties of other components. Since pharmaceutical dosage components such as binders, diluents, antiadherents, surfactants and the like may adversely interact with the active ingredient compound, a stabilizing means is required for effective pharmaceutical dosages.

Therefore, it is an object of the present invention to provide a stable solid peroral pharmaceutical formulation comprising substituted pyrrolyl substituted pyran ring-opened hydroxy acids for therapy of hypercholesterolemia or hyperlipidemia. More particularly, it is the object of the present invention to provide a stable solid peroral pharmaceutical formulation comprising a HMG CoA reductase inhibitor, such as the aforedescribed CI-981 Hemi-Calcium, as active ingredient.

SUMMARY OF THE INVENTION

Accordingly, the present invention provides a pharmaceutical formulation characterized by improved stability of a 7-substituted pyrrolyl-3,5-dihydroxyheptanoic acid salt as active ingredient combined with at least one pharmaceutically acceptable stabilizing additive for peroral treatment of hypercholesterolemia or hyperlipidemia.

An aspect of the present invention is to provide a stable oral pharmaceutical formulation for the treatment of hypercholesterolemia or hyperlipidemia comprising as active ingredient, a HMG-CoA reductase enzyme inhibitor according to Formula (I), as defined above, which is stabilized by combination with at least one pharmaceutically acceptable metal salt additive.

Another aspect of the present invention is to provide a stable oral pharmaceutical formulation for the treatment of hypercholesterolemia or hyperlipidemia comprising, as an active ingredient, a HMG-CoA reductase inhibitor such as CI-981 Hemi-Calcium namely the enantiomer [R-(R*,R*)]-2-(4-fluorophenyl-$\beta,\delta$-dihydroxy-5-(1-methylethyl)-3-phenyl-4-[(phenylamino)carbonyl)]-1H-pyrrole-1-heptanoic acid, hemicalcium salt, having the proposed isomeric structural Formula (IA) stabilized by a combination with at least one pharmaceutically acceptable alkaline earth metal salt such as calcium carbonate, calcium hydroxide, magnesium carbonate, magnesium hydroxide, magnesium silicate, magnesium aluminate or aluminum magnesium hydroxide.

Further, a preferred embodiment of the present invention provides a stable peroral pharmaceutical formulation for the treatment of hypercholesterolemia or hyperlipidemia comprising the HMG-CoA reductase inhibitor, CI-981 Hemi-Calcium, having the proposed structure according to the above-described structural Formula (IA) combined with calcium carbonate as stabilizing additive.

Further, a preferred embodiment of the present invention provides a stable oral pharmaceutical formulation for the treatment of hypercholesterolemia or hyperlipidemia comprising the HMG-CoA reductase inhibitor, CI-981 Hemi-Calcium, as active ingredient in a composition comprising, in addition to the stabilizing additive calcium carbonate, at least one other ingredient such as a binder, diluent, disintegrant, surfactant, and, optionally, antioxidant.

More specifically, the present invention provides a stable solid oral pharmaceutical composition wherein the active ingredient dosage is between about 1% and about 50% by weight of the composition.

The present invention also provides a stable solid oral pharmaceutical composition containing about 5% to about 75% of the stabilizer calcium carbonate by weight of the composition.

Another preferred embodiment of the present invention is a stable solid oral pharmaceutical composition comprising in addition to the active and the stabilizing ingredients, cited above, by weight, between about 5% and about 75% microcrystalline cellulose; between about 1% and about 80% of hydrous lactose; between about 1% and about 15% of croscarmellose sodium; between about 0.5% and about 6% hydroxypropyl cellulose; between about 0.1% and about 4% of Tween 80; between about 0.25% and about 2% of magnesium stearate; and optionally between about 0.0% and about 3% of sodium ascorbate or butylated hydroxyanisole of the total solid composition.

The present invention is also directed to a method of preparing a stable solid composition of the active ingredient according to Formula (I) comprising a stabilizing additive, for peroral therapy of hypercholesterolemia or hyperlipidemia.

A preferred embodiment of the present invention also provides a method for preparing the solid oral composition, including stabilizing the active ingredient, CI-981 Hemi-Calcium, according to Formula (IA) with calcium carbonate and admixing a binder, a diluent, a disintegrant, a surfactant, and optionally an antioxidant.

DETAILED DESCRIPTION OF THE INVENTION

The pyran ring-opened hydroxy acid corresponding to certain trans-6-[2-(3 or 4-carboxamido-substituted pyrrol-1-yl)alkyl]-4-hydroxypyran-2-ones can be useful inhibitors of HMG-CoA reductase and may be used in their free acid form. Both lactone and free acid forms can be prepared in accordance with the process described in U.S. Pat. No. 4,681,893, which is incorporated by reference therefor. The free acid can be prepared by hydrolysis of the lactone form or by treatment of the salt with cationic exchange resin ($H^+$ resin) and evaporating the water portion. These free acids also react to form pharmaceutically acceptable metal or amine salts. The term "pharmaceutically acceptable metal salt" contemplates sodium, potassium, lithium, calcium, magnesium, aluminum, iron, or zinc salts. The term "pharmaceutically acceptable amine salt" contemplates salts formed by reaction with ammonium hydroxide or organic amine salt or for example methylglucamine, choline, arginine, 1-deoxy-2-(methylamino)-D-glucitol and the like.

Insofar as the hydroxy acid compounds according to formula I or metal or amine salts thereof are HMG-CoA reductase inhibitors they may be useful in the treatment of hypercholesterolemia or hyperlipidemia. The compound of particular interest is the HMG-CoA reductase enzyme inhibitor, CI-981 Hemi-Calcium, Formula (IA), which is presently under development as a drug for treatment of hypercholesterolemia or hyperlipidemia.

The preferred compounds according to the present invention, especially the compound CI-981 or [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid hemicalcium salt, inhibit the biosynthesis of cholesterol as measured in the CSI screen assay disclosed in U.S. Pat. No. 4,681,893, which is incorporated by reference. More particularly, the level of HMG-CoA reductase enzyme activity in standard laboratory rats is increased by feeding the rats a chow diet containing 5% cholestyramine for four days, after which the rats are sacrificed. The rat livers are dissected and homogenized, and the incorporation of cholesterol—$^{14}$C-acetate into nonsaponifiable lipid by the rat liver homogenate is measured. The micromolar concentration of compound required for 50% inhibition of sterol synthesis over a one-hour period is measured, and denoted as an $IC_{50}$ value. The activity data of representative examples of the compound CI-981 Hemi-Calcium, its enantiomer and the racemate of both compounds have been disclosed in the aforementioned U.S. Pat. No. 5,273,995, which are incorporated herein.

| Compound | $IC_{50}$ (micromoles/liter) |
|---|---|
| [R-(R*R*)] isomer (CI-981 Hemi-Calcium) | 0.0044 |
| [S-(R*R*)] isomer | 0.44 |
| Racemate | 0.045 |

The most preferred compound of the present invention, CI-981 (structural Formula IA), is the enantiomer [R-(R*R*)]-2-(4-fluorophenyl)-β,δ-dihydroxy-5-(1-methylethyl)-3-phenyl-4-[(phenylamino)carbonyl]-1H-pyrrole-1-heptanoic acid, hemicalcium salt. This chiral form can be synthesized from known starting materials or from materials prepared according to methods analogous to known processes in accordance with the scheme 2 of the copending patent application recited above and incorporated by reference herein, as follows:

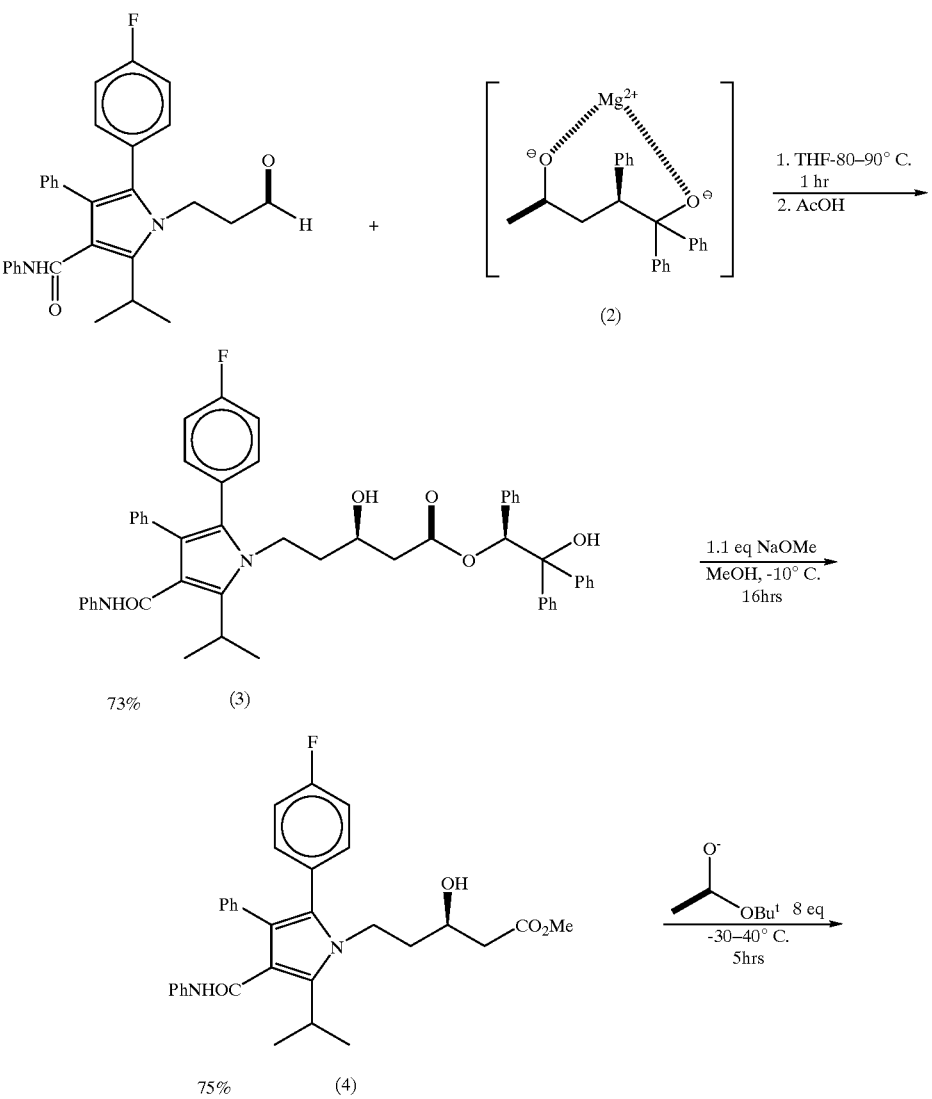

-continued

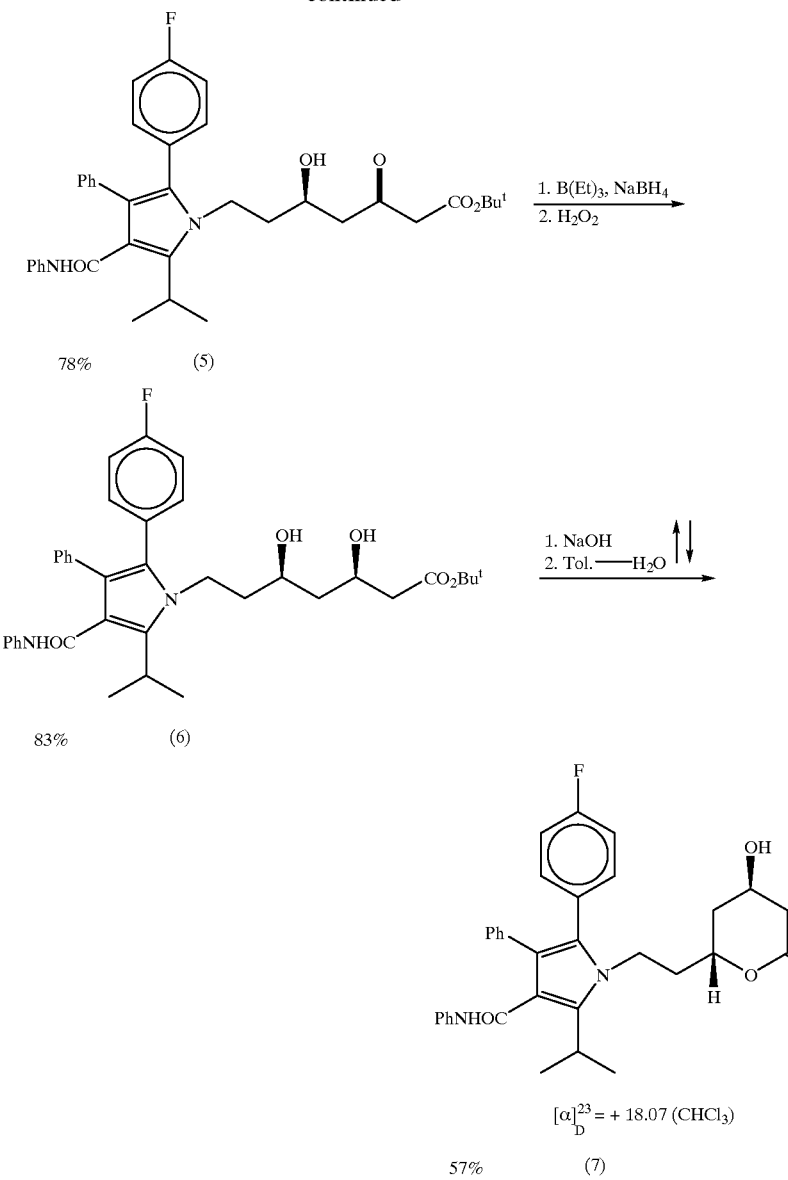

In addition, the preferred chiral form can be prepared from a racemic mixture prepared by the methods described in U.S. Pat. No. 4,681,893, especially examples 1 and 2 which description is incorporated by reference therefor.

Reference of the racemate and separation of the preferred isomer can be performed in accordance with the methodology for chiral synthesis disclosed in U.S. Pat. No. 5,273,995, as illustrated in the Examples 1–5, which is incorporated herein by reference therefor.

The present invention provides a pharmaceutical composition containing hypocholesterolemic or hypolipidemic compounds according to preferredly Formula (I) or more preferredly Formula (IA). The preferred effective stereoisomeric compounds of the present invention are administered to the patient at adult dosage levels of from approximately 10 to 500 mg per day, or from about 0.1 to about 8.0 mg/kg body weight per day. More preferred daily dosages range from about 0.5 to about 1.0 mg/kg. The unit dosage treatment embodiment provided by the present invention for oral or parenteral administration may be varied or adjusted from 10 to 500 mg, preferably from 20 to 100 mg depending on potency or application.

Since the hydroxy acid compounds according to formula I are susceptible to degradation to the lactone form in an acidic environment, it has been necessary to stabilize their structural integrity in pharmaceutical formulations. Moreover, the compounds have been determined to decompose rapidly under the impact of UV and fluorescent light.

For the purpose of stable oral preparations of the present invention, pharmaceutically acceptable inert carriers can be either solid or liquid. The most preferred embodiment of the present invention provides for an oral solid formulation which may include powders, tablets, dispersible granules, capsules, and cachets. A solid carrier may be one or more substances which can also act as diluents, flavoring agents, binders, or tablet disintegrating agents. Encapsulating materials are also within the scope of the present invention.

In powdered preparations, the carrier is preferably a solid which is finely divided in a homogeneous mixture with the finely divided active ingredient. In tablets, the active component is blended with the carrier material with binding properties that facilitate compacting, shaping and sizing as desirable. Oral powders or tablets according to the present invention are generally designed to contain between about 1% to about 50% by weight of the active ingredient.

As is usual in the art, pharmaceutical preparations are in suitable unit dosage form, which can be a capsule, cachet or tablet, or any number thereof, as appropriate. Dosages are held to be within the skill of the art and may vary with the particular requirements and bioavailability of the active ingredient.

In practice, use of the salt form amounts to use of the acid or lactone form. Appropriate pharmaceutically acceptable salts within the scope of the invention are those derived from bases such as sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine and the like.

Preferably, the lithium, calcium, magnesium, aluminum and ferrous or ferric salts are prepared from the sodium or potassium salt by adding the appropriate reagent to a solution of the sodium or potassium salt, i.e., addition of calcium chloride to a solution of the sodium or potassium salt of the compound of the formula I will give the calcium salt thereof.

The active hydroxy acid metal salt ingredient of the present invention which may be an isomeric compound with a structure according to Formula (I) or, preferredly, Formula (IA) can be prepared from sodium salt or lactone as illustrated in Example A, below.

EXAMPLE A

Calcium Salt from Sodium Salt and/or Lactone

One mole lactone (540.6 g) is dissolved in 5 L of MeOH; after dissolution 1 L $H_2O$ is added. While stirring, one equivalent NaOH is added and the reaction is followed by HPLC until 2% or less lactone and methyl ester of the diolacid remains (one cannot use an excess of NaOH, because $Ca(OH)_2$ will form on addition of $CaCl_2$). Usually NaOH is charged as caustic (51.3 ml, 0.98 eq.) or as pellets (39.1 g, 0.98 eq.).

The above procedure is shown as follows:

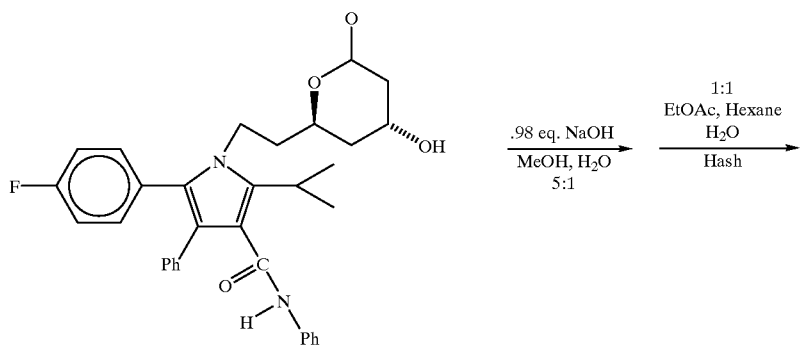

m.w. = 540.6 g

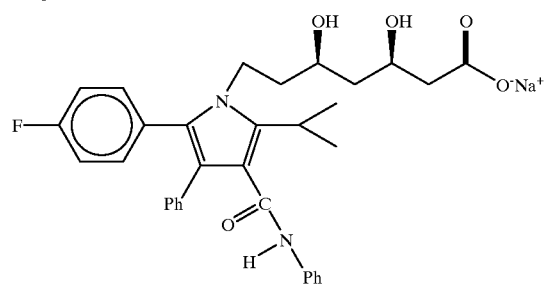

The abbreviation "Ph" is for the term phenyl group. Upon completion of hydrolysis, 10 L $H_2O$ are added, then the product is washed at least two times with a 1:1 mixture of EtOAc/Hexane. Each wash should contain 10 L each of EtOAc/Hexane. If sodium salt is pure, 15 L of MeOH are added. If it is impure and/or contains color, 100 g of G-60 charcoal are added, the mixture is stirred for two hours, filtered over supercel, and washed with 15 L MeOH. An assay analysis (weight per volume, %) is performed on the reaction mixture by HPLC, to determine the exact amount of salt in solution.

Subsequently, about ½ equivalent or a slight excess of CaCl$_2$2H$_2$O (73.5 g) is dissolved in 20 L H$_2$O. Both the reaction mixture and the CaCl$_2$ solution are heated to 60° C. CaCl$_2$ solution is added slowly, with high agitation. After complete addition, the reaction mixture is cooled slowly to 15° C. and filtered. The filter cake is washed with 5 L H$_2$O and dried at 50° C. in a vacuum oven.

The product can be recrystallized by dissolving in 4 L of EtOAc (50° C.) filtering over supercel, washing with 1 L EtOAc, then charging 3 L of hexane to the 50° C. reaction solution.

The above procedure is shown as follows:

(IA). The solid formulation according to the present invention also includes, in addition to a stabilizing metal or alkaline earth metal salt, several additives which are known as suitable agents in the art comprising combinations and concentrations as further described below.

The present invention without limiting further provides for diluent additives such as microcrystalline cellulose, hydrous lactose, corn starch, sucrose, silicic anhydride or polysaccharides (as are known as suitable in the art); binders such as methyl cellulose, carboxymethylcellulose, hydroxypropylcellulose, hydroxymethylpropylcellulose, polyvinylpyrrolidone, polyvinylalcohol or starch; disinte-

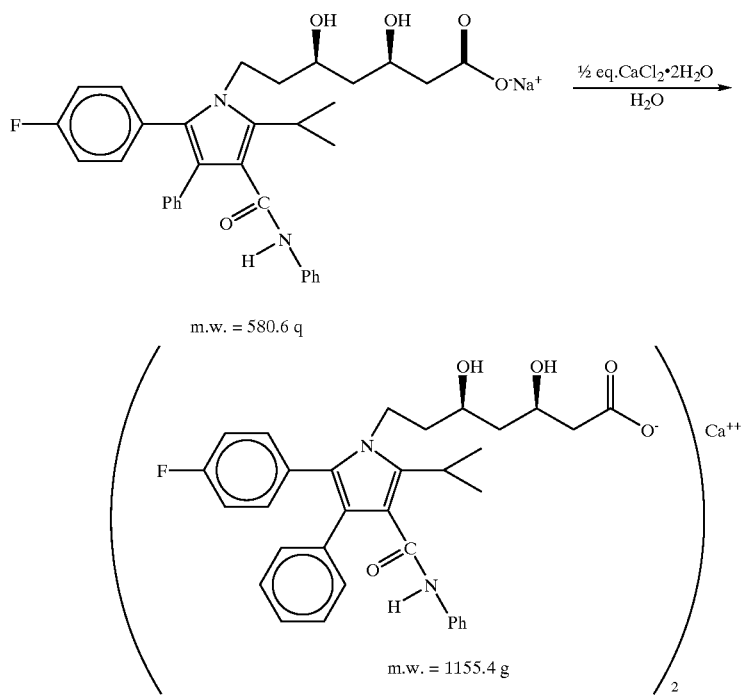

The present invention provides a preferred composition for stabilizing the active ingredient such as, e.g., CI-981 Hemi-Calcium, using basic inorganic pharmaceutically acceptable salts of calcium such as calcium carbonate and calcium hydroxide or basic inorganic pharmaceutically acceptable salts of magnesium such as magnesium carbonate, magnesium hydroxide, magnesium silicate, magnesium aluminate, and aluminum magnesium hydroxide, or basic inorganic pharmaceutically acceptable salts of lithium such as lithium hydroxide and similar lithium compounds or other similarly suitable alkaline earth metals. The basic inorganic salts of calcium, lithium or magnesium can be utilized in a weight ratio ranging between about 0.1 to 1 and about 50 to 1 of salt compound to active ingredient.

Stabilized solid oral pharmaceutical formulations of the present invention are designed to protect the anti-hypercholesterolemia or anti-hyperlipidemia drug, e.g., CI-981 Hemi-Calcium, of Formula IA (as defined above), from any degrading or processing environment, as well as preserve it from photochemical decomposition during storage. Specifically, the most preferred active chemical ingredient is the compound CI-981 Hemi-Calcium of Formula grants such as carboxymethylcellulose calcium, croscarmellose sodium, or starch; and surfactants such as Tween 80 or polyoxyethylene-polyoxypropylene copolymer.

Antioxidants can also be incorporated with the formulations in order to prevent any oxidation of the drug compound. For example, antioxidants that could be used are butylated hydroxanisole, sodium ascorbate, butylated hydroxytoluene, sodium metabisulfate, malic acid, citric acid and ascorbic acid.

The most preferred embodiment of the present invention is directed to a solid oral composition including CI-981 Hemi-Calcium as active ingredient, calcium carbonate as the stabilizing component, and other additives.

The basic excipient, calcium carbonate, has been found to provide effective control of the microenvironment of the composition. Further to the present invention, microcrystalline cellulose and hydrous lactose are applied as suitable diluents. In addition, the inventive composition contains a suitable amount of croscarmellose sodium as functional disintegrant. The non-ionic detergent Tween 80 is used as a surfactant. The composition also contains hydroxypropyl cellulose as binder selected from among several applicable substances such as, i.e., polyethylene glycol, polyvinylpyrrolidone, polyvinyl alcohol, hydroxymethylcellulose or hydroxypropylmethylcellulose. As anti-oxidants, reagents such as butylated hydroxyanisole, sodium ascorbate, ascorbic acid or others may optionally be incorporated in the composition. Magnesium stearate can be selected from a group including other substances such as stearic acid, palmitic acid, talc or similar lubricating compounds.

Other possible and supplemental ingredients such as preservatives, driers, glidants, or colorants known as conventional by those skilled in the art may be included optionally in the inventive formulation.

In accordance with the preferred embodiment of the present invention, the formulations provide for the following concentration ranges of ingredients by weight: the active ingredient or drug concentration is in the range from about 1% to about 50%; calcium carbonate from about 5% to about 75%; microcrystalline cellulose from about 5% to about 75%; hydrous lactose from about 1% to about 80%; croscarmellose sodium from about 1% to about 15%; hydroxypropylcellulose from about 0.5% to about 6%; Tween 80 from about 0.1% to about 4%; magnesium stearate from about 0.25% to about 2%; and sodium ascorbate [or ascorbic acid] from about 0.0% to about 3%.

The more preferred composition formulated according to the present invention includes the following approximate concentrations of ingredients by weight: 6.91% of the drug; 22% of calcium carbonate; 40% microcrystalline cellulose; 22.19% hydrous lactose; 6% croscarmellose sodium; 2% hydroxypropyl cellulose; 0.4% Tween 80; and 0.5% magnesium stearate; in addition, optionally 0.02% of an anti-oxidant such as sodium ascorbate.

In particular, CI-981 Hemi-Calcium degrades rapidly in compositions prepared by the wet-granulation method. It has therefore been a surprising discovery that, by adding calcium carbonate, solid formulations for this drug can be prepared by the wet granulation method without compromising the stability of the drug.

Method of Preparation of Pharmaceutical Composition:

The method for preparing a solid pharmaceutical composition according to the present invention includes (a) milling an excess of the drug, which can be a compound of Formula I or Formula IA (CI-981 Hemi-Calcium); (b) dissolving at least one binder additive in aqueous surfactant solution; (c) blending the milled drug with at least one drug-stabilizing additive and at least one diluent additive with the drug-stabilizing additive and one half of a disintegrant additive in a rotary mixing vessel equipped with a chopping device; (d) granulating the blended drug ingredient mixture of step (c) with the surfactant/binder solution of step (b) in gradual increments in the chopper equipped mixing vessel; (e) drying the granulated drug mixture overnight at about 50° C.; (f) sieving the dried granulated drug mixture; (g) tumble blending the sieved drug mixture with the remaining amount of the disintegrant additive; (h) mixing separately an aliquot of the drug mixture of step (g) with magnesium stearate, sieving same, and returning same to the drug mixture of step (g) and tumble blending the entire drug mixture; and compressing aliquots of the drug mixture of step (h) into tablet having suitable drug strength.

More particularly, the preferred embodiments of the present invention can be prepared in accordance with the batch procedure given in the examples below.

EXAMPLE 1 (PROTOCOL)

In order to produce 1.5 kg of the composition formulated for peroral therapy, the following steps are taken:

(a) An excess of about 5% by weight of CI-981 Hemi-Calcium is passed through a Model D Fitzmill, which is equipped with a No. 0 RH screen (0.027"). The mill is run at a high speed with impact forward. Exactly 103.65 g of the milled drug is weighed for step (c).

(b) Tween 80 in an appropriate amount (6.0 g) is dissolved in 100 ml of purified water heated to about 50° C. and mixed for approximately 5 minutes; similarly the hydroxypropyl cellulose (30.0 g) is dispersed in the warm Tween 80 solution and mixed for about 5 minutes; the remaining purified water (500 ml) is added, and the entire mixture is then allowed to hydrate for at least 4 (four) hours.

(c) Thereafter, the milled drug, CI-981 Hemi-Calcium (103.65 g), calcium carbonate (330.0 g), microcrystalline cellulose (600.0 g), hydrous lactose (332.85 g), and 50% of the croscarmellose sodium (45.0 g) are mixed in the 10 liter-Collette Gral for about 5 minutes with the mixer running at 300 rpm and chopper speed 1.

(d) The blended preparation of step (c) is granulated with the solution of step (b) by adding the solution over 30 to 60 seconds with only the mixer running at 300 rpm; then the mixing is continued up to a total of 3 minutes with the mixer speed of 300 rpm and the chopper speed set at 1; the bowl is now lowered and material scraped from the blades and the top of the mixing apparatus. Subsequently, the preparation is remixed for another 3 minutes with the mixer running 300 rpm and the chopper speed setting at 1, with additional amounts of purified water and 3 minutes time increments of mixing, as necessary to obtain adequate granular consistency.

(e) The granulated preparation is spread on paper-lined trays, dried at 50° C. overnight to a load only of approximately 2%.

(f) The dried granulation is passed through a Quadromill (Comill) which is equipped with a 0.032" screen.

(g) Approximately half the milled granulation is transferred to a 4 qt. twin shell blender, followed by the remaining 50% (w/w) of the croscarmellose sodium (45.0 g) and finally the remaining milled granulation; the entire mixture is tumble blended for 10 minutes.

(h) Approximately 50 g of the blend resulting from step (g) is removed and mixed with magnesium stearate (7.50 g); this side mixture is passed through a #40 mesh screen and returned to the 4 qt. twin shell blender, and the entire mixture is tumble blended for 5 minutes.

(i) Finally, an appropriate aliquot of the final mixture is compressed to obtain a tablet weight containing the desired drug strength.

EXAMPLE 2

All steps in this Example 2 are the same as in Example 1 except for step (b) which proceeds as follows:

(2b) Firstly, Tween 80 (6.0 g) is dissolved in 100 ml of purified water which has been heated to 50° C.; secondly, after about 5 minutes of mechanical stirring, the hydroxypropyl cellulose (30.0 g) is dispersed in the Tween 80 solution and further mixed for about 5 minutes; thirdly (and optionally) sodium ascorbate (0.3 g) is dissolved in the remaining volume of purified water and added to the Tween 80-hydroxypropyl cellulose mixture. Thereupon the mixture is allowed to hydrate for at least four (4) hours.

EXAMPLE 3

All steps of this alternative embodiment are as described in Example 1 with the exception of process step (b). However, step (b) is as follows:

Firstly, Tween 80 is dissolved in 100 ml of purified water which has been heated to 50° C. Secondly, butylated hydroxyanisole is dissolved in 10 ml of ethanol; which solution is then stirred into the Tween 80 mixture and agitated for 5 minutes. Thirdly, the hydroxypropyl cellulose is dispersed in the above mixture and stirred for approximately 5 minutes. The remaining purified water is added to the mixture which is then allowed to hydrate for at least 4 hours.

The tablets as prepared in all the Examples are film-coated with a film-coating agent known to those of skill in the art to about a 3% weight increase.

The comparative stability of the preferred antihypercholesterolemia or antihyperlipidemia formulations containing CI-981 was tested under highly accelerated stress conditions at elevated temperatures. In particular, the stability of a CI-981 formulation was tested by comparing a powder blend prepared according to the method of Example 3, at 2.5 mg active ingredient dosage in the presence (Ex. 4) or the absence (Ex. 5) of calcium carbonate. The samples were stored in duplicate for two and four weeks at either 45° or 60° C. and then analyzed by reverse phase high performance liquid chromatography ("HPLC"). The HPLC assay procedure employs a Zorbax® Reliance C18 column (8 cm long, 5 micron bead) and a mobile phase of acetonitrile in aqueous buffer (35:65) containing triethylamine, sodium acetate adjusted to pH 4.0. A detection wavelength of 244 nm was used.

The results showed that the calcium carbonate containing preparation of Example 4 incurred no detectable losses of the drug CI-981 after two weeks at 60° C. and only negligible losses of about 0.25% by weight after four weeks at 45° C. and about one half percent by weight at 60° C. In contrast, the formulation of Example 5, lacking calcium carbonate, lost by weight about 2.45% ingredient after four weeks storage at 45° C., about 4.12% of CI-981 after only two weeks and about 5.3% at 60° C. (See Table I).

The second set of comparative data (see Table II) concerns the formulations of Examples 6 and 7 prepared in accord with the protocol of Example 3, wherein the composition was packaged in a capsule at 2.5 mg strength with calcium carbonate (Ex. 6) and without calcium carbonate (Ex. 7). The formulation of Example 6, when measured by HPLC, lost about one half a percent by weight of CI-981 after four weeks at 45° C. and about 2.2% after two weeks at 60° C. The capsule preparation of Example 7 had a

TABLE I

Stability of CI-981 formulations: a powder blend with (Example 4) and without (Example 5) calcium carbonate.

| | PERCENT DRUG REMAINING | | | |
|---|---|---|---|---|
| | Ex. 4 | | Ex. 5 | |
| TIME (WEEKS) | 45° C. | 60° C. | 45° C. | 60° C. |
| 0 | 100 | 100 | 100 | 100 |
| 2 | ND | 100 | 100 | 95.88 |
| 4 | 99.75 | 99.48 | 97.55 | 94.7 |

ND = not determined

TABLE II

Stability of CI-981 formulations: a capsule with (Example 6) and without (Example 7) calcium carbonate.

| | PERCENT DRUG REMAINING | | | |
|---|---|---|---|---|
| | Ex. 6 | | Ex. 7 | |
| TIME (WEEKS) | 45° C. | 60° C. | 45° C. | 60° C. |
| 0 | 100 | 100 | 100 | 100 |
| 2 | ND | 97.81 | ND | 86 |
| 4 | 99.55 | ND | 95.6 | ND |

ND = not determined

TABLE III

Stability of CI-981 formulations: a coated tablet with calcium carbonate (Example 8).

| | PERCENT DRUG REMAINING | |
|---|---|---|
| TIME (WEEKS) | 45° C. | 60° C. |
| 0 | 100 | 100 |
| 2 | ND | 99.11 |
| 4 | 99.47 | 98.30 |

ND = not determined

CI-981 content which was diminished by about 4.4% after four weeks at 45° C. After two weeks at 60° C., about 14% of CI-981 Hemi-Calcium was lost, as measured by HPLC.

Finally, the stability of the preferred formulation according to the present invention was tested in the form of a coated tablet (Example 8) containing calcium carbonate (see Table III). In particular, the preparation of Example 8 was stored for four weeks at 45° C. and lost about 0.5% by weight of CI-981. After two weeks at 60° C., the composition (Ex. 8) contained about 0.9% less by weight active ingredient and after four weeks at 60° C. about 1.7% less by weight active ingredient. Clearly, the formulation according to the preferred embodiment containing calcium carbonate effectively protects the integrity of the active compounds during both the wet granulation step of the process of preparing the stable solid composition and the subsequent storage in the form of a powder blend, capsule or coated tablet.

Consequently, any variations of the invention described above are not to be regarded as a departure from the spirit and scope of the invention as claimed.

What is claimed is:

1. A pharmaceutical composition for the peroral treatment of hypercholesterolemia or hyperlipidemia characterized by improved stability comprising in a mixture, about 1% to about 50% by weight of the composition of a compound as active ingredient of structural formula I

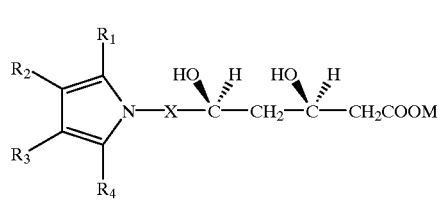

formula I wherein X is —CH$_2$—, —CH$_2$CH$_2$—, —CH$_2$CH$_2$CH$_2$— or —CH$_2$CH(CH$_3$)1

R$_1$ is 1-naphthyl; 2-naphthyl; cyclohexyl, norbornenyl; 2-,3-, or 4-pyridinyl; phenyl; phenyl substituted with fluorine, chlorine, bromine, hydroxyl, trifluoromethyl, alkyl of from one to four carbon atoms, alkoxy of from one to four carbon atoms, or alkanoylalkoxy of from two to eight carbon atoms;

either R$_2$ or R$_3$ is ——CONR$_5$R$_6$ where R$_5$ and R$_6$ are independently hydrogen; alkyl of from one to six carbon atoms; 2-,3-, or 4-pyridinyl; phenyl; phenyl substituted with fluorine, chlorine, bromine, cyano, trifluoromethyl, or carboalkoxy of from three to eight carbon atoms; and the other of R$_2$ or R$_3$ is hydrogen; alkyl of from one to six carbon atoms; cyclopropyl; cyclobutyl; cyclopentyl; cyclohexyl; phenyl; or phenyl substituted with fluorine, chlorine, bromine, hydroxyl, trifluoromethyl, alkyl of from one to four carbon atoms, alkoxy of from one to four carbon atoms, or alkanoyloxy of from two to eight carbon atoms;

R$_4$ is alkyl of from one to six carbon atoms, cyclopropyl, cyclobutyl, cyclopentyl, cyclohexyl, or trifluoromethyl;

M is a pharmaceutically acceptable metal salt; and about 5% to about 75% by weight of the composition of calcium carbonate to stabilize the composition.

2. The stable pharmaceutical composition of claim 1, wherein M is a pharmaceutically acceptable alkaline earth metal salt.

3. The stable pharmaceutical composition of claim 2, wherein the alkaline earth metal salt is selected from the group consisting of calcium carbonate, calcium hydroxide, magnesium carbonate, magnesium hydroxide, magnesium silicate, magnesium aluminate and aluminum magnesium hydroxide.

4. A pharmaceutical composition characterized by improved stability comprising in a mixture, about 1% to about 50% by weight of the composition of a pharmaceutically acceptable metal salt of [R—R*,R*)]-2-(4-fluorophenyl-β, Λ-dihydroxy-5-(1-methylethyl)-3-phenyl-4-[(phenylamino)carbonyl]-1H-pyrrole-1-heptanoic acid; and about 5% to about 75% by weight of the composition of calcium carbonate to stabilize the composition.

5. The stable pharmaceutical composition of claim 4, wherein the pharmaceutically acceptable metal salt is an alkaline earth metal salt.

6. The stable pharmaceutical composition of claim 5, wherein the alkaline earth metal salt is selected from the group consisting of calcium carbonate, calcium hydroxide, magnesium carbonate, magnesium hydroxide, magnesium silicate, magnesium aluminate and aluminum magnesium hydroxide.

7. A pharmaceutical composition characterized by improved stability comprising in a mixture, the Hemi-Calcium of Formula (IA):

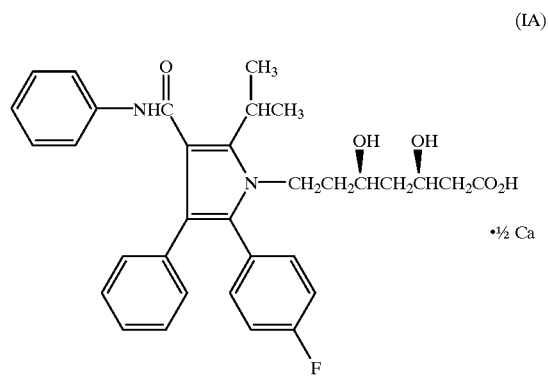

and an effective amount of calcium carbonate.

8. A method of improving the stability of a pharmaceutical composition comprising as an active ingredient a compound having the structural formula I

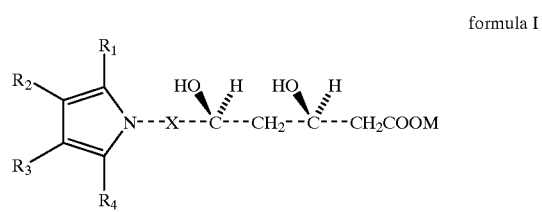

formula I wherein X is —CH$_2$—, —CH$_2$CH$_2$—, —CH$_2$CH$_2$CH$_2$— or —CH$_2$CH(CH$_3$);

R$_1$ is 1-naphthyl; 2-naphthyl; cyclohexyl, norbornenyl; 2-,3-, or 4-pyridinyl; phenyl; phenyl substituted with fluorine, chlorine, bromine, hydroxyl, trifluoromethyl, alkyl of from one to four carbon atoms, alkoxy of from one to four carbon atoms, or alkanoylalkoxy of from two to eight carbon atoms;

either R$_2$ or R$_3$ is ——CONR$_5$R$_6$ where R$_5$ and R$_6$ are independently hydrogen; alkyl of from one to six carbon atoms; 2-3- or 4-pyridinyl; phenyl; phenyl substituted with fluorine, chlorine, bromine, cyano, trifluoromethyl, or carboalkoxy of from three to eight carbon atoms; and the other of R$_2$ or R$_3$ is hydrogen; alkyl of from one to six carbon atoms; cyclopropyl; cyclobutyl; cyclopentyl; cyclohexyl; phenyl; or phenyl substituted with fluorine, chlorine, bromine, hydroxyl, trifluoromethyl, alkyl of from one to four carbon atoms, alkoxy of from one to four carbon atoms, or alkanoyloxy of from two to eight carbon atoms;

R$_4$ is alkyl of from one to six carbon atoms, cyclopropyl, cyclobutyl, cyclopentyl, cyclohexyl, or trifluoromethyl;

M is a pharmaceutically acceptable metal salt;

by adding an effective amount of an alkaline earth metal salt to the composition.

9. The method of claim 8, wherein the alkaline earth metal salt is selected from the group consisting of calcium carbonate, calcium hydroxide, magnesium carbonate, magnesium hydroxide, magnesium silicate, magnesium aluminate and aluminum magnesium hydroxide.

10. The method of claim 9, wherein the alkaline earth metal salt is calcium carbonate.

11. The method of claim 8, wherein M is a pharmaceutically acceptable alkaline earth metal salt.

12. The method of claim 11, wherein the alkaline earth metal salt is selected from the group consisting of calcium carbonate, calcium hydroxide, magnesium carbonate, magnesium hydroxide, magnesium silicate, magnesium aluminate and aluminum magnesium hydroxide.

13. A method of improving the stability of a pharmaceutical composition by adding an effective amount of calcium carbonate to a composition comprising a pharmaceutically acceptable metal salt of [R—R*,R*)]-2-(4-fluorophenyl-β,δ-dihydroxy-5-(1-methylethyl)-3-phenyl-4-[(phenylamino)carbonyl]-1H-pyrrole-1 heptanoic acid.

14. The method of claim 13, wherein the pharmaceutically acceptable metal salt is an alkaline earth metal salt.

15. The method of claim 14, wherein the alkaline earth metal salt is selected from the group consisting of calcium carbonate, calcium hydroxide, magnesium carbonate, magnesium hydroxide, magnesium silicate, magnesium aluminate and aluminum magnesium hydroxide.

16. A method of improving the stability of a pharmaceutical composition by adding an effective amount of calcium carbonate to a composition comprising the Hemi-Calcium of Formula (IA):

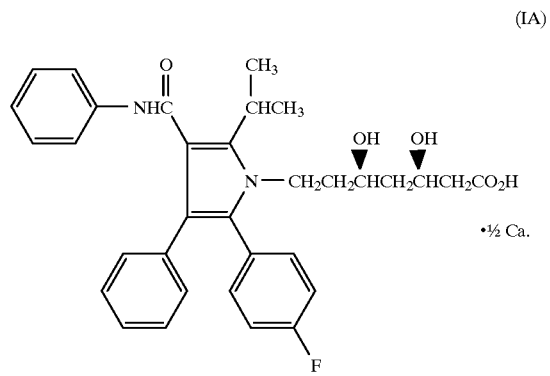

(IA)

17. A pharmaceutical composition for the peroral treatment of hypercholesterolemia or hyperlipidemia characterized by improved stability comprising in a mixture, about 1% to about 50% by weight of the composition of a compound as active ingredient of structural formula I

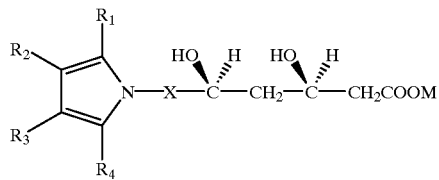

formula I wherein X is —$CH_2$—, —$CH_2CH_2$—, —$CH_2CH_2CH_2$— or —$CH_2CH(CH_3)$1

$R_1$ is 1-naphthyl; 2-naphthyl; cyclohexyl, norbornenyl; 2-,3-, or 4-pyridinyl; phenyl; phenyl substituted with fluorine, chlorine, bromine, hydroxyl, trifluoromethyl, alkyl of from one to four carbon atoms, alkoxy of from one to four carbon atoms, or alkanoylalkoxy of from two to eight carbon atoms;

either $R_2$ or $R_3$ is ———$CONR_5R_6$ where $R_5$ and $R_6$ are independently hydrogen; alkyl of from one to six carbon atoms; 2-,3-, or 4-pyridinyl; phenyl; phenyl substituted with fluorine, chlorine, bromine, cyano, trifluoromethyl, or carboalkoxy of from three to eight carbon atoms; and the other of $R_2$ or $R_3$ is hydrogen; alkyl of from one to six carbon atoms; cyclopropyl; cyclobutyl; cyclopentyl; cyclohexyl; phenyl; or phenyl substituted with fluorine, chlorine, bromine, hydroxyl, trifluoromethyl, alkyl of from one to four carbon atoms, alkoxy of from one to four carbon atoms, or alkanoyloxy of from two to eight carbon atoms;

$R_4$ is alkyl of from one to six carbon atoms, cyclopropyl, cyclobutyl, cyclopentyl, cyclohexyl, or trifluoromethyl;

M is a pharmaceutically acceptable metal salt; and about 5% to about 75% by weight of the composition of at least one stabilizing pharmaceutically acceptable calcium or lithium salt additive.

18. The stable pharmaceutical composition of claim 17 wherein the active ingredient is a pharmaceutically acceptable metal salt of [R—(R*,R*)]-2-(4-fluorophenyl-β,δ-dihydroxy-5(1-methylethyl)-3-phenyl-4-[(phenylamino)carbonyl]-1H-pyrrole-1-heptanoic acid.

19. The stable pharmaceutical composition of claim 17 wherein the stabilizing pharmaceutically acceptable additive is a calcium salt.

* * * * *

UNITED STATES PATENT AND TRADEMARK OFFICE
CERTIFICATE OF CORRECTION

PATENT NO. : 6,126,971
DATED : October 3, 2000
INVENTOR(S) : Mills et al.

It is certified that error appears in the above-identified patent and that said Letters Patent is hereby corrected as shown below:

<u>Title page,</u>
Item [75], Inventors, insert -- Jr. -- after the name "Nesbitt"

<u>Column 14,</u>
Line 39, "load only" should read -- load-only dose --

Signed and Sealed this

Ninth Day of July, 2002

Attest:

Attesting Officer

JAMES E. ROGAN
*Director of the United States Patent and Trademark Office*